(12) United States Patent
Santos

(10) Patent No.: US 9,370,150 B2
(45) Date of Patent: Jun. 21, 2016

(54) COTTON VARIETY 11R124B2R2

(71) Applicant: Monsanto Technology LLC, St. Louis, MO (US)

(72) Inventor: Albert Santos, Scott, MS (US)

(73) Assignee: Monsanto Technology LLC, St. Louis, MO (US)

( * ) Notice: Subject to any disclaimer, the term of this patent is extended or adjusted under 35 U.S.C. 154(b) by 303 days.

(21) Appl. No.: 13/912,013

(22) Filed: Jun. 6, 2013

(65) Prior Publication Data

US 2014/0007269 A1    Jan. 2, 2014

Related U.S. Application Data

(60) Provisional application No. 61/666,888, filed on Jul. 1, 2012.

(51) Int. Cl.
*A01H 1/00* (2006.01)
*A01H 5/10* (2006.01)
*C12N 15/82* (2006.01)

(52) U.S. Cl.
CPC .............. *A01H 5/10* (2013.01); *C12N 15/8245* (2013.01); *C12N 15/8247* (2013.01); *C12N 15/8271* (2013.01); *C12N 15/8274* (2013.01); *C12N 15/8275* (2013.01); *C12N 15/8278* (2013.01); *C12N 15/8279* (2013.01); *C12N 15/8286* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 4,940,835 A | 7/1990 | Shah | |
| 5,338,544 A | 8/1994 | Donovan | |
| 5,451,514 A | 9/1995 | Boudet et al. | |
| 5,523,520 A | 6/1996 | Hunsperger et al. | |
| 5,633,435 A | 5/1997 | Barry | |
| 5,981,834 A | 11/1999 | John et al. | |
| 6,329,570 B1 | 12/2001 | Martineau | |
| 6,740,488 B2 | 5/2004 | Rangwala et al. | |
| 6,893,826 B1 | 5/2005 | Hillyard et al. | |
| 7,087,818 B2 * | 8/2006 | Keim | 800/314 |
| 7,105,729 B2 | 9/2006 | Mitchell et al. | |
| 7,223,907 B2 | 5/2007 | Huber et al. | |
| 7,381,861 B2 | 6/2008 | Cerny et al. | |
| 7,626,095 B2 * | 12/2009 | Fraser et al. | 800/314 |
| 7,858,764 B1 | 12/2010 | Huber et al. | |
| 8,071,735 B2 | 12/2011 | Cerny et al. | |
| 2011/0143346 A1 | 6/2011 | Huber et al. | |
| 2012/0149024 A1 | 6/2012 | Cerny et al. | |

FOREIGN PATENT DOCUMENTS

WO    WO 2004/072235    8/2004

OTHER PUBLICATIONS

Bowman et al., "Pedigrees of Upland and Pima Cotton Cultivars Released Between 1970 2005," Mississippi Agricultural & Forestry Experiment Station, Bulletin 1155, Dec. 2006.
Eshed et al., "Less-than-addictive epistatic interactions of quantitative trait loci in tomato," *Genetics*, 143:1807-1817, 1996.
Fehr (ed), "Backcross Method," In: Principles of Cultivar Development, vol. 1: Theory and Technique, pp. 360-376, 1987.
Kraft et al., "Linkage disequilibrium and fingerprinting in sugar beet," *Theor. Appl. Genet.*, 101:323-326, 2000.
Poehlman (ed), "Breeding Corn (Maize)," In Breeding Field Crops, 3rd Ed., AVI Publishing Company, Westport, Connecticut, pp. 469-481, 1987.
Poehlman (eds), "Backcross Breeding," In: Breeding Field Crops, 4th Ed., pp. 172-175, 1995.
Rieger et al., In: Glossary of Genetics and Cytogenetics, Classical and Molecular, Springer-Verlag, Berlin, p. 116, 1976.
Sprague et al. (Eds.), "8-1.1.2 Backcrossing," In: Corn and Improvement, $3^{rd}$ Ed., Madison, WI, pp. 472-473, 1998.
Marchosky et al., "Bollgard® and Bollgard II® Efficacy in Near Isogenic Lines of 'DP50' Upland Cotton in Arizona," Arizona Cotton Report, The University of Arizona College of Agriculture and Life Sciences, 2001.
Phipps et al., "Performance of Roundup Flex© cotton varieties in the North Mississippi River Delta," pp. 874-880, 2006 Beltwide Cotton Conferences, San Antonio, Texas, Jan. 3-6, 2006.
Virginia Cotton Production Guide 2011, College of Agriculture and Life Sciences, Virginia Tech, 2011.
U.S. PVP Application for Cotton Variety 11R124B2R2, dated Jul. 19, 2012.
Variety specific information as indicated in transmittal letter of Jan. 24, 2014 Information Disclosure Statement for U.S. Appl. No. 13/912,013.

* cited by examiner

*Primary Examiner* — Mykola Kovalenko
(74) *Attorney, Agent, or Firm* — Dentons US LLP

(57) ABSTRACT

The invention relates to the novel cotton variety designated 11R124B2R2. Provided by the invention are the seeds, plants, plant parts and derivatives of the cotton variety 11R124B2R2. Also provided by the invention are methods of using cotton variety 11R124B2R2 and products derived therefrom. Still further provided by the invention are methods for producing cotton plants by crossing the cotton variety 11R124B2R2 with itself or another cotton variety and plants and seeds produced by such methods.

22 Claims, No Drawings

COTTON VARIETY 11R124B2R2

This application claims the priority of U.S. Provisional Appl. Ser. No. 61/666,888, filed Jul. 1, 2012, the entire disclosure of which is incorporated herein by reference.

BACKGROUND OF THE INVENTION

1. Field of the Invention

The present invention relates generally to the field of cotton breeding. In particular, the invention relates to the novel cotton variety 11R124B2R2.

2. Description of Related Art

The goal of a commercial cotton breeding program is to develop new, unique and superior cotton varieties. In cotton, important traits include higher fiber (lint) yield, earlier maturity, improved fiber quality, resistance to diseases and insects, tolerance to drought and heat, and improved agronomic traits. The breeder initially selects and crosses two or more parental lines, followed by generation advancement and selection, thus producing many new genetic combinations. The breeder can theoretically generate billions of different genetic combinations via this procedure.

SUMMARY OF THE INVENTION

One aspect of the present invention relates to seed of the cotton variety 11R124B2R2. The invention also relates to plants produced by growing the seed of the cotton variety 11R124B2R2, as well as the derivatives of such plants. As used herein, the term "plant" includes plant cells, plant protoplasts, plant cells of a tissue culture from which cotton plants can be regenerated, plant calli, plant clumps, and plant cells that are intact in plants or parts of plants, such as pollen, flowers, seeds, bolls, leaves, stems, and the like.

Another aspect of the invention relates to a tissue culture of regenerable cells of the cotton variety 11R124B2R2, as well as plants regenerated therefrom, wherein the regenerated cotton plant expresses all the physiological and morphological characteristics of a plant grown from the cotton seed designated 11R124B2R2.

Yet another aspect of the current invention is a cotton plant of the cotton variety 11R124B2R2 comprising at least a first transgene, wherein the cotton plant is otherwise capable of expressing all the physiological and morphological characteristics of the cotton variety 11R124B2R2. In particular embodiments of the invention, a plant is provided that comprises a single locus conversion. A single locus conversion may comprise a transgenic gene which has been introduced by genetic transformation into the cotton variety 11R124B2R2 or a progenitor thereof. A transgenic or nontransgenic single locus conversion can also be introduced by backcrossing, as is well known in the art. In certain embodiments of the invention, the single locus conversion may comprise a dominant or recessive allele. The locus conversion may confer potentially any desired trait upon the plant as described herein.

Still yet another aspect of the invention relates to a first generation ($F_1$) hybrid cotton seed produced by crossing a plant of the cotton variety 11R124B2R2 to a second cotton plant. Also included in the invention are the $F_1$ hybrid cotton plants grown from the hybrid seed produced by crossing the cotton variety 11R124B2R2 to a second cotton plant. Still further included in the invention are the seeds of an $F_1$ hybrid plant produced with the cotton variety 11R124B2R2 as one parent, the second generation ($F_2$) hybrid cotton plant grown from the seed of the $F_1$ hybrid plant, and the seeds of the $F_2$ hybrid plant.

In a further aspect of the invention, a composition is provided comprising a seed of cotton variety 11R124B2R2 comprised in plant seed growth media. In certain embodiments, the plant seed growth media is a soil or synthetic cultivation medium. In specific embodiments, the growth medium may be comprised in a container or may, for example, be soil in a field. Plant seed growth media are well known to those of skill in the art and include, but are in no way limited to, soil or synthetic cultivation medium. Advantageously, plant seed growth media can provide adequate physical support for seeds and can retain moisture and/or nutritional components. Examples of characteristics for soils that may be desirable in certain embodiments can be found, for instance, in U.S. Pat. Nos. 3,932,166 and 4,707,176. Synthetic plant cultivation media are also well known in the art and may, in certain embodiments, comprise polymers or hydrogels. Examples of such compositions are described, for example, in U.S. Pat. No. 4,241,537.

Still yet another aspect of the invention is a method of producing cotton seeds comprising crossing a plant of the cotton variety 11R124B2R2 to any second cotton plant, including itself or another plant of the variety 11R124B2R2. In particular embodiments of the invention, the method of crossing comprises the steps of a) planting seeds of the cotton variety 11R124B2R2; b) cultivating cotton plants resulting from said seeds until said plants bear flowers; c) allowing fertilization of the flowers of said plants; and, d) harvesting seeds produced from said plants.

Still yet another aspect of the invention is a method of producing hybrid cotton seeds comprising crossing the cotton variety 11R124B2R2 to a second, distinct cotton plant which is nonisogenic to the cotton variety 11R124B2R2. In particular embodiments of the invention, the crossing comprises the steps of a) planting seeds of cotton variety 11R124B2R2 and a second, distinct cotton plant, b) cultivating the cotton plants grown from the seeds until the plants bear flowers; c) cross pollinating a flower on one of the two plants with the pollen of the other plant, and d) harvesting the seeds resulting from the cross pollinating.

Still yet another aspect of the invention is a method for developing a cotton plant in a cotton breeding program comprising: obtaining a cotton plant, or its parts, of the variety 11R124B2R2; and b) employing said plant or parts as a source of breeding material using plant breeding techniques. In the method, the plant breeding techniques may be selected from the group consisting of recurrent selection, mass selection, bulk selection, backcrossing, pedigree breeding, genetic marker-assisted selection and genetic transformation. In certain embodiments of the invention, the cotton plant of variety 11R124B2R2 is used as the male or female parent.

Still yet another aspect of the invention is a method of producing a cotton plant derived from the cotton variety 11R124B2R2, the method comprising the steps of: (a) preparing a progeny plant derived from cotton variety 11R124B2R2 by crossing a plant of the cotton variety 11R124B2R2 with a second cotton plant; and (b) crossing the progeny plant with itself or a second plant to produce a progeny plant of a subsequent generation which is derived from a plant of the cotton variety 11R124B2R2. In one embodiment of the invention, the method further comprises: (c) crossing the progeny plant of a subsequent generation with itself or a second plant; and (d) repeating steps (b) and (c) for at least 2-10 additional generations to produce an inbred cotton plant derived from the cotton variety 11R124B2R2.

Also provided by the invention is a plant produced by this and the other methods of the invention. Plant variety 11R124B2R2-derived plants produced by this and the other methods of the invention described herein may, in certain embodiments of the invention, be further defined as comprising the traits of plant variety 11R124B2R2 given in Table 1.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides, in one aspect, methods and composition relating to plants, seeds and derivatives of the cotton variety 11R124B2R2. The cotton variety 11R124B2R2 has been judged to be uniform for breeding purposes and testing. The variety can be reproduced by planting and growing seeds of the variety under self-pollinating or sib-pollinating conditions, as is known to those of skill in the agricultural arts. Variety 11R124B2R2 shows no variants other than what would normally be expected due to environment or that would occur for almost any characteristic during the course of repeated sexual reproduction. The results of an objective description of the variety are presented below, in Table 1. Those of skill in the art will recognize that these are typical values that may vary due to environment and that other values that are substantially equivalent are within the scope of the invention.

Breeding History

Monsanto has developed 11R124B2R2 insect-protected and herbicide-tolerant cotton through conventional breeding. The donor parent was DP 491 B2RF containing Bollgard II® (MON 531, 15985), and Roundup Ready® Flex (MON 88913). MON 531 and MON 15985 produce the Cry1Ac and Cry2Ab2 proteins, respectively, and provide protection from feeding damage caused by lepidopteron insect pests. Cry1Ac and Cry2Ab2 are *Bacillus thuringiensis* (subsp. *Kurstaki*) proteins. MON 88913 produces a 5-enolpyruvylshikimate-3-phosphate synthase protein from *Agrobacterium* sp. strain CP4 (CP4 EPSPS), which confers tolerance to glyphosate, the active ingredient in the Roundup® family of agricultural herbicides.

11R124B2R2 was developed through backcross breeding using 01X06 as the recurrent parent. The $F_1$, $BC_1$, and $BC_2$ crosses were made in Monsanto Company's greenhouse in Scott, Miss. $BC_2F_1$ plants were grown and selfed in Monsanto Company's greenhouse in Scott, Miss. $BC_2F_2$ plants were grown and selfed in the field near Canas, Costa Rica. Plant selection 01X06*3/DP491[B1][B2][R2]@>@>@.389. was found to be homozygous for the gene insertions MON 15985 and 88913 and advanced to a progeny row.

01X06*3/DP491[B1][B2][R2]@>@>@.389. was planted in progeny rows in Scott, Miss. in May, 2007. Progeny rows were evaluated for gene purity, homozygosity and trueness to type of the recurrent parent 01X06. 01X06*3/DP491[B1][B2][R2]@>@>@.389. was selected for increase in Scott, Miss. in 2008 and given the experimental name 09X469B2R2. Selections were based on lint yield, lint percent, and acceptable fiber qualities. 09X469B2R2 was sent to winter nursery in Costa Rica for increase during the 2008-09 season. In 2009, 09X469B2R2 was increased in Scott, Miss.

09X469B2R2 was evaluated Beltwide in replicated research plots in 2008, 2009, and 2010 in the Advanced Testing Program. 09X469B2R2 was given the pre-commercial name 11R124B2R2 in 2011 and further evaluated in yield trials Beltwide.

TABLE 1

| Phenotypic Description of Variety 11R124B2R2 |
| --- |
| Species: *Gossypium hirsutum* L |
| Areas of Adaptation: |
| Eastern |
| Delta |
| Central |
| Plains |
| Western |
| Arizona |
| General: |
| Plant Habit: Intermediate |
| Foliage: Intermediate |
| Stem Lodging: Intermediate |
| Fruiting Branch: Normal |
| Growth: Intermediate |
| Leaf Color: Medium green |
| Boll Shape: Length more than width |
| Boll Breadth: Broadest at middle |
| Maturity: |
| Days till maturity: 112 |
| Plant: |
| Cm to 1$^{st}$ Fruiting Branch (from cotyledonary node): 23.6 |
| No. of Nodes to 1$^{st}$ Fruiting Branch (excluding cotyledonary node): 7.65 |
| Mature Plant Height (from cotyledonary node to terminal): 96.2 |
| Leaf (Upper most, fully expanded leaf): |
| Type: Normal |
| Pubescence: Sparse |
| Stem: |
| Stem Pubescence: Intermediate |
| Glands: |
| Leaf: Normal |
| Stem: Normal |
| Calyx lobe (normal is absent): Normal |
| Flower: |
| Petals: Cream |
| Pollen: Cream |
| Petal Spot: Absent |
| Seed: |
| Seed Index (g/100 seeds, fuzzy basis): 9.04 |
| Lint Index (g lint/100 seeds): 6.71 |
| Boll: |
| Lint percent, picked: 42.9 |
| Number of seeds per boll: 26.4 |
| Grams Seed Cotton per Boll: 4.48 |

TABLE 1-continued

Phenotypic Description of Variety 11R124B2R2

Number of Locules per Boll: 4-5
Boll Type: Open
Fiber Properties:

Method (HVI or other): HVI
Length (inches, 2.5% SL): 1.15
Uniformity (%): 83.44
Strength, T1 (g/tex): 29.1
Elongation, E1 (%): 7.7
Micronaire: 4.7

TABLE 1-continued

Phenotypic Description of Variety 11R124B2R2

Nematodes, Insects and Pests:

Bollworm: Resistant
Cotton Leafworm: Resistant
Pink bollworm: Resistant
Tobacco bud worm: Resistant These are typical values. Values may vary due to environment. Other values that are substantially equivalent are within the scope of the invention.

The performance characteristics of cotton variety 11R124B2R2 were also analyzed and comparisons were made with competing varieties. The results of the analysis are presented below, in Table 2.

TABLE 2

Performance Data for Variety 11R124B2R2

| Entries Compared | BLSZ | BOP | EL | FMATR | FOR | LFHAR | LNTH | LP | LTAC |
|---|---|---|---|---|---|---|---|---|---|
| 11R124B2R2 | 4 | 65 | 7.7 | 87.1 | 1.5 | 6 | 1.15 | 42.9 | 1,575 |
| DP 0935 B2RF | 4.5 | 60 | 6.9 | 88.1 | 1.5 | 5 | 1.13 | 41.4 | 1,513 |
| Deviation | −0.42 | 4.39 | 0.76 | −0.98 | −0.07 | 1 | 0.02 | 1.5 | 62.01 |
| Significance | ** | * | ** | ** | | | ** | ** | * |
| # Obs | 17 | 25 | 41 | 41 | 10 | 2 | 41 | 82 | 78 |
| Years | 2 | 2 | 2 | 2 | 2 | 1 | 2 | 2 | 2 |
| Win Percent | 71 | 25 | 95 | 7 | 50 | 0 | 80 | 87 | 63 |
| Test Mean | 4 | 63 | 7.1 | 87.6 | 2.2 | 5.3 | 1.16 | 41.3 | 1,458 |
| 11R124B2R2 | 3.7 | 63 | 7.4 | 86.6 | 1.8 | | 1.13 | 42.9 | 1,599 |
| DP 1050 B2RF | 3.7 | 60 | 7.5 | 86.6 | 2.4 | | 1.16 | 43.2 | 1,456 |
| Deviation | −0.01 | 3.26 | −0.03 | 0.04 | −0.67 | | −0.03 | −0.35 | 143.3 |
| Significance | | * | | | | | ** | + | ** |
| # Obs | 6 | 14 | 25 | 25 | 3 | | 25 | 55 | 53 |
| Years | 1 | 1 | 1 | 1 | 1 | | 1 | 1 | 1 |
| Win Percent | 67 | 14 | 36 | 48 | 100 | | 12 | 53 | 68 |
| Test Mean | 3.8 | 62 | 7 | 87.1 | 2.5 | | 1.15 | 41.3 | 1,473 |
| 11R124B2R2 | 3.7 | 63 | 7.4 | 86.6 | 1.8 | | 1.13 | 42.9 | 1,600 |
| DP 1048 B2RF | 3.8 | 63 | 7.2 | 86.7 | 2.6 | | 1.16 | 41.8 | 1,507 |
| Deviation | −0.13 | 0.16 | 0.28 | −0.1 | −0.78 | | −0.02 | 1.08 | 92.83 |
| Significance | | | * | | | | ** | ** | ** |
| # Obs | 6 | 14 | 25 | 25 | 3 | | 25 | 55 | 53 |
| Years | 1 | 1 | 1 | 1 | 1 | | 1 | 1 | 1 |
| Win Percent | 67 | 27 | 64 | 36 | 100 | | 12 | 78 | 58 |
| Test Mean | 3.8 | 62 | 7 | 87.1 | 2.5 | | 1.15 | 41.3 | 1,472 |
| 11R124B2R2 | | 81 | 6.6 | 87 | 2.3 | | 1.14 | 41.3 | 1,664 |
| DP 1044 B2RF | | 80 | 7.2 | 87.2 | 3.3 | | 1.13 | 39.4 | 1,627 |
| Deviation | | 0.42 | −0.55 | −0.11 | −1 | | 0.01 | 1.83 | 36.67 |
| Significance | | | * | | | | | ** | |
| # Obs | | 4 | 9 | 9 | 1 | | 9 | 18 | 17 |
| Years | | 1 | 1 | 1 | 1 | | 1 | 1 | 1 |
| Win Percent | | 50 | 22 | 22 | 100 | | 67 | 89 | 59 |
| Test Mean | | 79 | 6.2 | 87.7 | 3 | | 1.16 | 40.1 | 1,528 |
| 11R124B2R2 | 3.7 | 63 | 7.4 | 86.6 | 1.8 | | 1.13 | 42.9 | 1,601 |
| DP 1034 B2RF | 3.9 | 64 | 7.5 | 86.7 | 3.1 | | 1.16 | 42.6 | 1,534 |
| Deviation | −0.21 | −0.13 | −0.07 | −0.1 | −1.33 | | −0.03 | 0.24 | 66.47 |
| Significance | | | | | | | ** | | * |
| # Obs | 6 | 14 | 25 | 25 | 3 | | 25 | 55 | 54 |
| Years | 1 | 1 | 1 | 1 | 1 | | 1 | 1 | 1 |
| Win Percent | 83 | 33 | 40 | 48 | 100 | | 20 | 74 | 57 |
| Test Mean | 3.8 | 62 | 7 | 87.1 | 2.5 | | 1.15 | 41.3 | 1,472 |
| 11R124B2R2 | 3.5 | 63 | 7.5 | 86.6 | 1.8 | | 1.13 | 42.9 | 1,599 |
| DP 1032 B2RF | 3.6 | 64 | 6.2 | 87.5 | 2.8 | | 1.16 | 42.8 | 1,573 |
| Deviation | −0.1 | −0.79 | 1.24 | −0.97 | −1 | | −0.03 | 0.02 | 25.56 |
| Significance | | | ** | ** | | | ** | | |
| # Obs | 5 | 14 | 25 | 25 | 3 | | 25 | 55 | 54 |
| Years | 1 | 1 | 1 | 1 | 1 | | 1 | 1 | 1 |
| Win Percent | 80 | 45 | 100 | 4 | 100 | | 20 | 69 | 56 |
| Test Mean | 3.7 | 62 | 7 | 87.1 | 2.5 | | 1.15 | 41.3 | 1,475 |
| 11R124B2R2 | | 81 | 6.6 | 87 | 2.3 | | 1.14 | 41.3 | 1,664 |
| DP 1028 B2RF | | 78 | 6.5 | 87.7 | 3 | | 1.15 | 43.2 | 1,673 |
| Deviation | | 2.25 | 0.12 | −0.67 | −0.67 | | −0.02 | −1.95 | −9.44 |
| Significance | | | | ** | | | | ** | |
| # Obs | | 4 | 9 | 9 | 1 | | 9 | 18 | 17 |
| Years | | 1 | 1 | 1 | 1 | | 1 | 1 | 1 |
| Win Percent | | 33 | 56 | 11 | 100 | | 22 | 0 | 41 |
| Test Mean | | 79 | 6.2 | 87.7 | 3 | | 1.16 | 40.1 | 1,528 |

TABLE 2-continued

Performance Data for Variety 11R124B2R2

| | | | | | | | | | |
|---|---|---|---|---|---|---|---|---|---|
| 11R124B2R2 | 4 | 65 | 7.7 | 87.1 | 1.5 | 6 | 1.15 | 42.9 | 1,574 |
| DP 164 B2RF | 4.1 | 59 | 6 | 88.4 | 2.1 | 5 | 1.19 | 38.1 | 1,311 |
| Deviation | −0.11 | 5.98 | 1.65 | −1.29 | −0.62 | 1 | −0.04 | 4.75 | 262.73 |
| Significance | | ** | ** | ** | * | | ** | ** | ** |
| # Obs | 16 | 25 | 39 | 39 | 10 | 2 | 39 | 80 | 76 |
| Years | 2 | 2 | 2 | 2 | 2 | 1 | 2 | 2 | 2 |
| Win Percent | 56 | 14 | 100 | 5 | 100 | 0 | 13 | 100 | 88 |
| Test Mean | 4 | 63 | 7.1 | 87.6 | 2.2 | 5.3 | 1.17 | 41.3 | 1,450 |
| 11R124B2R2 | 4.2 | 70 | 7.5 | 87.6 | 1.5 | 6 | 1.16 | 42.3 | 1,568 |
| DP 161 B2RF | 3.9 | 63 | 6 | 89.2 | 1.6 | 5 | 1.21 | 37.6 | 1,331 |
| Deviation | 0.29 | 7.38 | 1.58 | −1.52 | −0.17 | 1 | −0.05 | 4.71 | 237.43 |
| Significance | | ** | ** | ** | | ** | ** | ** | ** |
| # Obs | 11 | 15 | 24 | 24 | 8 | 2 | 24 | 43 | 39 |
| Years | 1 | 2 | 2 | 2 | 2 | 1 | 2 | 2 | 2 |
| Win Percent | 36 | 14 | 100 | 0 | 100 | 0 | 4 | 100 | 87 |
| Test Mean | 4.1 | 68 | 6.9 | 88.1 | 2.1 | 5.3 | 1.18 | 40.9 | 1,454 |
| 11R124B2R2 | 4.2 | 70 | 7.7 | 87.6 | 1.5 | 6 | 1.16 | 42.8 | 1,608 |
| DP 143 B2RF | 4.4 | 62 | 6.2 | 88.3 | 1.8 | 6 | 1.23 | 37.3 | 1,312 |
| Deviation | −0.16 | 7.87 | 1.5 | −0.75 | −0.35 | 0 | −0.07 | 5.45 | 296.1 |
| Significance | | + | ** | + | + | | ** | ** | ** |
| # Obs | 11 | 13 | 22 | 22 | 8 | 2 | 22 | 36 | 33 |
| Years | 1 | 2 | 2 | 2 | 2 | 1 | 2 | 2 | 2 |
| Win Percent | 64 | 11 | 100 | 18 | 83 | — | 0 | 100 | 91 |
| Test Mean | 4.1 | 67 | 7.1 | 88.1 | 2.1 | 5.3 | 1.18 | 40.9 | 1,481 |
| 11R124B2R2 | 4.2 | 70 | 7.5 | 87.6 | 1.5 | 6 | 1.16 | 42.2 | 1,578 |
| DP 141 B2RF | 4.3 | 64 | 6.3 | 88.5 | 2.1 | 5 | 1.21 | 38.9 | 1,492 |
| Deviation | −0.05 | 6 | 1.24 | −0.85 | −0.67 | 1 | −0.05 | 3.33 | 86.24 |
| Significance | | + | ** | ** | + | | ** | ** | * |
| # Obs | 11 | 15 | 24 | 24 | 8 | 2 | 24 | 44 | 40 |
| Years | 1 | 2 | 2 | 2 | 2 | 1 | 2 | 2 | 2 |
| Win Percent | 73 | 17 | 100 | 4 | 100 | 0 | 8 | 98 | 68 |
| Test Mean | 4.1 | 68 | 6.9 | 88.1 | 2.1 | 5.3 | 1.18 | 40.8 | 1,459 |
| 11R124B2R2 | 4 | 65 | 7.7 | 87.1 | 1.5 | 6 | 1.15 | 42.9 | 1,575 |
| ST 5458B2RF | 4.5 | 64 | 6.4 | 88.9 | 2.6 | 5 | 1.15 | 39.6 | 1,546 |
| Deviation | −0.42 | 0.61 | 1.26 | −1.76 | −1.13 | 1 | −0 | 3.3 | 29.01 |
| Significance | * | | ** | ** | ** | | | ** | |
| # Obs | 17 | 25 | 39 | 39 | 10 | 2 | 39 | 81 | 77 |
| Years | 2 | 2 | 2 | 2 | 2 | 1 | 2 | 2 | 2 |
| Win Percent | 82 | 37 | 100 | 3 | 100 | 0 | 36 | 100 | 53 |
| Test Mean | 4 | 63 | 7.1 | 87.6 | 2.2 | 5.3 | 1.17 | 41.3 | 1,453 |
| 11R124B2R2 | 3.7 | 62 | 7.6 | 86.4 | 1.8 | | 1.13 | 43.4 | 1,624 |
| ST 5288B2RF | 3.8 | 63 | 6.9 | 87.7 | 2 | | 1.14 | 40.1 | 1,507 |
| Deviation | −0.11 | −1.53 | 0.74 | −1.29 | −0.22 | | −0.01 | 3.33 | 116.4 |
| Significance | | | ** | ** | | | | ** | ** |
| # Obs | 6 | 12 | 23 | 23 | 3 | | 23 | 47 | 46 |
| Years | 1 | 1 | 1 | 1 | 1 | | 1 | 1 | 1 |
| Win Percent | 50 | 50 | 100 | 0 | 100 | | 39 | 100 | 78 |
| Test Mean | 3.8 | 61 | 7.1 | 87 | 2.5 | | 1.15 | 41.4 | 1,492 |
| 11R124B2R2 | 4.2 | 70 | 7.7 | 87.6 | 1.5 | 6 | 1.16 | 42.8 | 1,608 |
| ST 4498B2RF | 4.3 | 70 | 8.1 | 86.6 | 2 | 5 | 1.16 | 38.8 | 1,435 |
| Deviation | −0.11 | 0.38 | −0.39 | 1.03 | −0.54 | 1 | 0 | 4 | 173.09 |
| Significance | | | ** | | * | | | ** | ** |
| # Obs | 11 | 13 | 22 | 22 | 8 | 2 | 22 | 36 | 33 |
| Years | 1 | 2 | 2 | 2 | 2 | 1 | 2 | 2 | 2 |
| Win Percent | 64 | 50 | 18 | 64 | 100 | 50 | 59 | 97 | 82 |
| Test Mean | 4.1 | 67 | 7.1 | 88.1 | 2.1 | 5.3 | 1.18 | 40.9 | 1,481 |
| 11R124B2R2 | 4 | 65 | 7.7 | 87.1 | 1.5 | 6 | 1.15 | 42.9 | 1,575 |
| PHY 485 WRF | 3.8 | 70 | 8 | 87 | 2.5 | 7 | 1.15 | 38.8 | 1,397 |
| Deviation | 0.2 | −5.48 | −0.36 | 0.14 | −1 | −1 | −0 | 4.06 | 177.59 |
| Significance | * | * | ** | | ** | ** | | ** | ** |
| # Obs | 17 | 25 | 40 | 40 | 10 | 2 | 40 | 81 | 77 |
| Years | 2 | 2 | 2 | 2 | 2 | 1 | 2 | 2 | 2 |
| Win Percent | 24 | 70 | 20 | 30 | 100 | 100 | 60 | 99 | 84 |
| Test Mean | 4 | 63 | 7.1 | 87.6 | 2.2 | 5.3 | 1.16 | 41.3 | 1,453 |
| 11R124B2R2 | | 81 | 6.6 | 87 | 2.3 | | 1.14 | 41.3 | 1,664 |
| PHY 375 WRF | | 80 | 5.7 | 88.1 | 3 | | 1.13 | 40.9 | 1,602 |
| Deviation | | 0.58 | 0.95 | −1.04 | −0.67 | | 0 | 0.37 | 61.67 |
| Significance | | | ** | ** | | | | | |
| # Obs | | 4 | 9 | 9 | 1 | | 9 | 18 | 17 |
| Years | | 1 | 1 | 1 | 1 | | 1 | 1 | 1 |
| Win Percent | | 50 | 100 | 0 | 100 | | 44 | 89 | 65 |
| Test Mean | | 79 | 6.2 | 87.7 | 3 | | 1.16 | 40.1 | 1,528 |

TABLE 2-continued

Performance Data for Variety 11R124B2R2

| Entries Compared | MIC | PHT | SFC | SOR | STR | TSCYD | UNIF | YLD_BE |
|---|---|---|---|---|---|---|---|---|
| 11R124B2R2 | 4.7 | 39.7 | 8.9 | 2.9 | 29.1 | 3,628 | 83.44 | 1,572 |
| DP 0935 B2RF | 5 | 39.6 | 8.9 | 2.9 | 29.5 | 3,626 | 83.39 | 1,514 |
| Deviation | −0.2 | 0.16 | −0.03 | 0.02 | −0.44 | 1.95 | 0.05 | 57.85 |
| Significance | ** | | | | ** | | | * |
| # Obs | 41 | 15 | 41 | 15 | 41 | 81 | 41 | 78 |
| Years | 2 | 2 | 2 | 2 | 2 | 2 | 2 | 2 |
| Win Percent | 85 | 57 | 56 | 40 | 39 | 43 | 51 | 56 |
| Test Mean | 4.8 | 41.7 | 8.4 | 3.8 | 30.3 | 3,509 | 83.89 | 1,457 |
| 11R124B2R2 | 4.8 | 41 | 9.2 | 2.7 | 28.9 | 3,731 | 83.1 | 1,596 |
| DP 1050 B2RF | 4.8 | 45.4 | 8.4 | 4.1 | 29.4 | 3,363 | 84.17 | 1,470 |
| Deviation | 0.02 | −4.34 | 0.79 | −1.37 | −0.53 | 368.59 | −1.07 | 126.26 |
| Significance | | ** | * | * | ** | ** | ** | ** |
| # Obs | 25 | 4 | 25 | 5 | 25 | 53 | 25 | 53 |
| Years | 1 | 1 | 1 | 1 | 1 | 1 | 1 | 1 |
| Win Percent | 48 | 100 | 8 | 100 | 32 | 68 | 4 | 66 |
| Test Mean | 4.9 | 42.6 | 8.6 | 4 | 30.4 | 3,569 | 83.75 | 1,472 |
| 11R124B2R2 | 4.8 | 41 | 9.2 | 2.7 | 28.9 | 3,729 | 83.1 | 1,597 |
| DP 1048 B2RF | 4.8 | 43.9 | 8.4 | 4.3 | 29.8 | 3,601 | 84.1 | 1,510 |
| Deviation | 0.06 | −2.86 | 0.82 | −1.6 | −0.88 | 128.71 | −1 | 87.05 |
| Significance | | + | ** | * | ** | + | ** | ** |
| # Obs | 25 | 4 | 25 | 5 | 25 | 53 | 25 | 53 |
| Years | 1 | 1 | 1 | 1 | 1 | 1 | 1 | 1 |
| Win Percent | 40 | 100 | 20 | 100 | 20 | 57 | 24 | 62 |
| Test Mean | 4.9 | 42.6 | 8.6 | 4 | 30.4 | 3,563 | 83.75 | 1,471 |
| 11R124B2R2 | 4.8 | | 9.4 | 2.3 | 28.8 | 4,008 | 83.27 | 1,666 |
| DP 1044 B2RF | 5 | | 8.5 | 3 | 29.4 | 4,130 | 83.71 | 1,627 |
| Deviation | −0.19 | | 0.85 | −0.67 | −0.67 | −122.31 | −0.44 | 38.57 |
| Significance | ** | | * | | | | * | |
| # Obs | 9 | | 9 | 1 | 9 | 17 | 9 | 17 |
| Years | 1 | | 1 | 1 | 1 | 1 | 1 | 1 |
| Win Percent | 100 | | 22 | 100 | 22 | 41 | 22 | 65 |
| Test Mean | 4.9 | | 8.3 | 3.2 | 30.6 | 3,806 | 84.24 | 1,527 |
| 11R124B2R2 | 4.8 | 41 | 9.2 | 2.7 | 28.9 | 3,730 | 83.1 | 1,598 |
| DP 1034 B2RF | 4.9 | 41.9 | 8.3 | 4.5 | 29.7 | 3,592 | 84.36 | 1,535 |
| Deviation | −0.05 | −0.86 | 0.9 | −1.77 | −0.81 | 138.56 | −1.26 | 63 |
| Significance | | | ** | * | ** | * | ** | * |
| # Obs | 25 | 4 | 25 | 5 | 25 | 54 | 25 | 54 |
| Years | 1 | 1 | 1 | 1 | 1 | 1 | 1 | 1 |
| Win Percent | 56 | 67 | 4 | 100 | 20 | 63 | 0 | 56 |
| Test Mean | 4.9 | 42.6 | 8.6 | 4 | 30.4 | 3,564 | 83.75 | 1,471 |
| 11R124B2R2 | 4.8 | 41 | 9.2 | 2.7 | 28.8 | 3,731 | 83.04 | 1,596 |
| DP 1032 B2RF | 4.8 | 44.9 | 8.7 | 5.1 | 30.6 | 3,669 | 83.58 | 1,571 |
| Deviation | −0.01 | −3.9 | 0.51 | −2.37 | −1.81 | 61.55 | −0.54 | 25.77 |
| Significance | | ** | * | * | ** | | * | |
| # Obs | 25 | 4 | 25 | 5 | 25 | 55 | 25 | 54 |
| Years | 1 | 1 | 1 | 1 | 1 | 1 | 1 | 1 |
| Win Percent | 56 | 100 | 20 | 100 | 0 | 60 | 24 | 54 |
| Test Mean | 4.9 | 42.6 | 8.6 | 4 | 30.3 | 3,578 | 83.75 | 1,475 |
| 11R124B2R2 | 4.8 | | 9.4 | 2.3 | 28.8 | 4,008 | 83.27 | 1,666 |
| DP 1028 B2RF | 5 | | 8 | 3 | 29.9 | 3,858 | 84.73 | 1,682 |
| Deviation | −0.22 | | 1.33 | −0.67 | −1.1 | 149.43 | −1.47 | −16.19 |
| Significance | ** | | ** | | * | | * | |
| # Obs | 9 | | 9 | 1 | 9 | 17 | 9 | 17 |
| Years | 1 | | 1 | 1 | 1 | 1 | 1 | 1 |
| Win Percent | 100 | | 11 | 100 | 22 | 59 | 22 | 41 |
| Test Mean | 4.9 | | 8.3 | 3.2 | 30.6 | 3,806 | 84.24 | 1,527 |
| 11R124B2R2 | 4.7 | 39.7 | 8.8 | 2.9 | 29.2 | 3,626 | 83.56 | 1,570 |
| DP 164 B2RF | 4.7 | 43.8 | 8.5 | 4 | 30.7 | 3,422 | 83.65 | 1,310 |
| Deviation | −0 | −4.07 | 0.31 | −1.08 | −1.5 | 203.94 | −0.09 | 259.76 |
| Significance | | ** | * | ** | ** | ** | | ** |
| # Obs | 39 | 15 | 39 | 15 | 39 | 80 | 39 | 76 |
| Years | 2 | 2 | 2 | 2 | 2 | 2 | 2 | 2 |
| Win Percent | 56 | 93 | 36 | 100 | 5 | 70 | 51 | 89 |
| Test Mean | 4.8 | 41.7 | 8.4 | 3.8 | 30.5 | 3,499 | 83.99 | 1,449 |
| 11R124B2R2 | 4.7 | 39.3 | 8.7 | 2.9 | 29.3 | 3,646 | 83.86 | 1,567 |
| DP 161 B2RF | 4.7 | 41.2 | 7.7 | 3.7 | 31.9 | 3,582 | 84.54 | 1,337 |
| Deviation | −0.05 | −1.92 | 0.93 | −0.8 | −2.6 | 64.09 | −0.68 | 229.29 |
| Significance | | | ** | * | ** | | ** | ** |
| # Obs | 24 | 11 | 24 | 11 | 24 | 43 | 24 | 39 |
| Years | 2 | 1 | 2 | 2 | 2 | 2 | 2 | 2 |
| Win Percent | 67 | 82 | 0 | 100 | 4 | 58 | 29 | 87 |
| Test Mean | 4.7 | 41.3 | 8.2 | 3.6 | 30.5 | 3,539 | 84.25 | 1,454 |

TABLE 2-continued

Performance Data for Variety 11R124B2R2

| | | | | | | | | |
|---|---|---|---|---|---|---|---|---|
| 11R124B2R2 | 4.7 | 39.3 | 8.7 | 2.9 | 29.3 | 3,687 | 83.95 | 1,604 |
| DP 143 B2RF | 4.4 | 41.1 | 8.4 | 3.5 | 31 | 3,459 | 83.73 | 1,302 |
| Deviation | 0.3 | −1.86 | 0.3 | −0.59 | −1.67 | 228.32 | 0.21 | 302.65 |
| Significance | ** | * | | * | ** | * | | ** |
| # Obs | 22 | 11 | 22 | 11 | 22 | 35 | 22 | 33 |
| Years | 2 | 1 | 2 | 2 | 2 | 2 | 2 | 2 |
| Win Percent | 5 | 90 | 36 | 89 | 5 | 63 | 68 | 88 |
| Test Mean | 4.7 | 41.3 | 8.3 | 3.6 | 30.6 | 3,562 | 84.25 | 1,481 |
| 11R124B2R2 | 4.7 | 39.3 | 8.7 | 2.9 | 29.3 | 3,670 | 83.86 | 1,576 |
| DP 141 B2RF | 4.6 | 43.8 | 8.4 | 3.9 | 31.5 | 3,758 | 83.72 | 1,494 |
| Deviation | 0.09 | −4.52 | 0.3 | −0.98 | −2.23 | −88.2 | 0.14 | 82.22 |
| Significance | + | ** | | ** | ** | | | * |
| # Obs | 24 | 11 | 24 | 11 | 24 | 42 | 24 | 40 |
| Years | 2 | 1 | 2 | 2 | 2 | 2 | 2 | 2 |
| Win Percent | 33 | 100 | 33 | 100 | 4 | 43 | 54 | 72 |
| Test Mean | 4.7 | 41.3 | 8.2 | 3.6 | 30.5 | 3,525 | 84.25 | 1,458 |
| 11R124B2R2 | 4.7 | 39.7 | 8.8 | 2.9 | 29.2 | 3,626 | 83.58 | 1,572 |
| ST 5458B2RF | 5.1 | 40.1 | 8.9 | 4.3 | 31.4 | 3,880 | 83.43 | 1,549 |
| Deviation | −0.37 | −0.37 | −0.03 | −1.39 | −2.16 | −253.79 | 0.16 | 23.17 |
| Significance | ** | | | ** | ** | ** | | |
| # Obs | 39 | 15 | 39 | 15 | 39 | 80 | 39 | 77 |
| Years | 2 | 2 | 2 | 2 | 2 | 2 | 2 | 2 |
| Win Percent | 95 | 50 | 51 | 100 | 0 | 32 | 67 | 51 |
| Test Mean | 4.8 | 41.7 | 8.4 | 3.8 | 30.5 | 3,499 | 84 | 1,452 |
| 11R124B2R2 | 4.8 | 41 | 9.3 | 2.7 | 28.9 | 3,754 | 83.11 | 1,620 |
| ST 5288B2RF | 5.1 | 42.1 | 8.7 | 3.3 | 29.3 | 3,770 | 83.29 | 1,503 |
| Deviation | −0.31 | −1.08 | 0.54 | −0.57 | −0.43 | −15.89 | −0.17 | 116.77 |
| Significance | ** | | ** | * | | | | ** |
| # Obs | 23 | 4 | 23 | 5 | 23 | 46 | 23 | 46 |
| Years | 1 | 1 | 1 | 1 | 1 | 1 | 1 | 1 |
| Win Percent | 87 | 100 | 22 | 100 | 35 | 33 | 39 | 80 |
| Test Mean | 4.9 | 42.6 | 8.7 | 4 | 30.4 | 3,605 | 83.7 | 1,491 |
| 11R124B2R2 | 4.7 | 39.3 | 8.7 | 2.9 | 29.3 | 3,687 | 83.95 | 1,604 |
| ST 4498B2RF | 4.6 | 37.5 | 7.9 | 4 | 32 | 3,591 | 84.63 | 1,440 |
| Deviation | 0.01 | 1.77 | 0.81 | −1.13 | −2.65 | 96.36 | −0.69 | 164.9 |
| Significance | | | ** | ** | ** | | ** | ** |
| # Obs | 22 | 11 | 22 | 11 | 22 | 35 | 22 | 33 |
| Years | 2 | 1 | 2 | 2 | 2 | 2 | 2 | 2 |
| Win Percent | 50 | 22 | 9 | 100 | 0 | 60 | 23 | 82 |
| Test Mean | 4.7 | 41.3 | 8.3 | 3.6 | 30.6 | 3,562 | 84.25 | 1,481 |
| 11R124B2R2 | 4.7 | 39.7 | 8.8 | 2.9 | 29.2 | 3,626 | 83.52 | 1,572 |
| PHY 485 WRF | 4.9 | 42.5 | 7.9 | 4.8 | 31.4 | 3,561 | 84.53 | 1,394 |
| Deviation | −0.17 | −2.76 | 0.99 | −1.87 | −2.21 | 64.95 | −1.02 | 177.28 |
| Significance | ** | ** | ** | ** | ** | | ** | ** |
| # Obs | 40 | 15 | 40 | 15 | 40 | 80 | 40 | 77 |
| Years | 2 | 2 | 2 | 2 | 2 | 2 | 2 | 2 |
| Win Percent | 78 | 87 | 5 | 100 | 2 | 52 | 12 | 83 |
| Test Mean | 4.8 | 41.7 | 8.4 | 3.8 | 30.4 | 3,499 | 83.94 | 1,452 |
| 11R124B2R2 | 4.8 | | 9.4 | 2.3 | 28.8 | 4,008 | 83.27 | 1,666 |
| PHY 375 WRF | 4.9 | | 8.5 | 4 | 29.8 | 3,914 | 84.06 | 1,603 |
| Deviation | −0.14 | | 0.89 | −1.67 | −1.03 | 93.53 | −0.8 | 63.14 |
| Significance | + | | | | | | * | |
| # Obs | 9 | | 9 | 1 | 9 | 17 | 9 | 17 |
| Years | 1 | | 1 | 1 | 1 | 1 | 1 | 1 |
| Win Percent | 67 | | 11 | 100 | 33 | 59 | 11 | 71 |
| Test Mean | 4.9 | | 8.3 | 3.2 | 30.6 | 3,806 | 84.24 | 1,527 |

**, *, +Significant at P < 0.01, 0.05, or 0.10, respectively

I. BREEDING COTTON VARIETY 11R124B2R2

One aspect of the current invention concerns methods for crossing the cotton variety 11R124B2R2 with itself or a second plant and the seeds and plants produced by such methods. These methods can be used for propagation of the cotton variety 11R124B2R2, or can be used to produce hybrid cotton seeds and the plants grown therefrom. A hybrid plant can be used as a recurrent parent at any given stage in a backcrossing protocol during the production of a single locus conversion of the cotton variety 11R124B2R2.

The variety of the present invention is well suited to the development of new varieties based on the elite nature of the genetic background of the variety. In selecting a second plant to cross with 11R124B2R2 for the purpose of developing novel cotton varieties, it will typically be desired to choose those plants which themselves exhibit one or more selected desirable characteristics. Examples of potentially desired characteristics include higher fiber (lint) yield, earlier maturity, improved fiber quality, resistance to diseases and insects, tolerance to drought and heat, and improved agronomic traits.

Any time the cotton variety 11R124B2R2 is crossed with another, different, variety, first generation ($F_1$) cotton progeny are produced. The hybrid progeny are produced regardless of characteristics of the two varieties produced. As such, an $F_1$ hybrid cotton plant may be produced by crossing 11R124B2R2 with any second cotton plant. The second cotton plant may be genetically homogeneous (e.g., inbred) or may itself be a hybrid. Therefore, any $F_1$ hybrid cotton plant produced by crossing cotton variety 11R124B2R2 with a second cotton plant is a part of the present invention.

Cotton plants can be crossed by either natural or mechanical techniques. Natural pollination occurs in cotton either by self pollination or natural cross pollination, which typically is aided by pollinating organisms. In either natural or artificial crosses, flowering and flowering time are important considerations.

The cotton flower is perfect in that the male and female structures are in the same flower. The crossed or hybrid seed can be produced by manual crosses between selected parents. Floral buds of the parent that is to be the female can be emasculated prior to the opening of the flower by manual removal of the male anthers. At flowering, the pollen from flowers of the parent plants designated as male, can be manually placed on the stigma of the previous emasculated flower. Seed developed from the cross is known as first generation ($F_1$) hybrid seed. Planting of this seed produces $F_1$ hybrid plants of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

Self-pollination occurs naturally in cotton with no manipulation of the flowers. For the crossing of two cotton plants, it may be beneficial to use artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a cotton flower include, for example, physical removal of the male parts, use of a genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed with forceps. Special care is required to remove immature buds that are hidden under the stipules at the leaf axil, and could develop into flowers at a later date. The flower is grasped between the thumb and index finger and the location of the stigma determined by examining the sepals. The calyx is removed by grasping a sepal with the forceps, pulling it down and around the flower, and repeating the procedure until the five sepals are removed. The exposed corolla is removed with care to avoid injuring the stigma. Cross-pollination can then be carried out using, for example, petri dishes or envelopes in which male flowers have been collected. Desiccators containing calcium chloride crystals can be used in some environments to dry male flowers to obtain adequate pollen shed.

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Cross-pollination is more common within rows than between adjacent rows; therefore, it may be beneficial to grow populations with genetic male sterility on a square grid to create rows in all directions. For example, single-plant hills on 50-cm centers may be used, with subdivision of the area into blocks of an equal number of hills for harvest from bulks of an equal amount of seed from male-sterile plants in each block to enhance random pollination.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include resistance to diseases and insects, tolerance to drought and heat, tolerance to herbicides, improvements in fiber traits and numerous other agronomic traits that may be desirable to the farmer or end user.

Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding is used to transfer one or a few favorable genes for a highly heritable trait into a desirable variety. This approach has been used extensively for breeding disease-resistant plant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Promising advanced breeding lines are thoroughly tested and compared to appropriate standards in environments representative of the commercial target area(s) for generally three or more years. The best lines are candidates for new commercial varieties. Those still deficient in a few traits may be used as parents to produce new populations for further selection.

These processes, which lead to the final step of marketing and distribution, may take as much as eight to 12 years from the time the first cross is made. Therefore, development of new varieties is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to one or more widely grown standard varieties. Single observations are generally inconclusive, while replicated observations provide a better estimate of genetic worth.

The goal of plant breeding is to develop new, unique and superior cotton varieties. The breeder initially selects and crosses two or more parental lines, followed by repeated selfing and selection, producing many new genetic combinations. Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same variety twice by using the exact same original parents and the same selection techniques. This unpredictability results in the expenditure of large amounts of research monies to develop superior new cotton varieties.

Pureline cultivars, such as generally used in cotton and many other crops, are commonly bred by hybridization of two or more parents followed by selection. The complexity of inheritance, the breeding objectives and the available resources influence the breeding method. The development of new varieties requires development and selection, the crossing of varieties and selection of progeny from superior crosses.

Pedigree breeding and recurrent selection breeding methods are used to develop varieties from breeding populations. Breeding programs combine desirable traits from two or more varieties or various broad-based sources into breeding pools from which varieties are developed by selfing and selection of desired phenotypes. The new varieties are evaluated to determine which have commercial potential.

Pedigree breeding is commonly used for the improvement of self-pollinating crops. Two parents which possess favorable, complementary traits are crossed to produce an $F_1$. An $F_2$ population is produced by selfing one or several $F_1$ plants. Selection of the best individuals may begin in the $F_2$ population or later depending upon objectives of the breeder; then, beginning in the $F_3$, the best individuals in the best families can be selected. Replicated testing of families can begin in the $F_3$ or $F_4$ generation to improve the effectiveness of selection for traits with low heritability. At an advanced stage of inbreeding (i.e., $F_6$ and $F_7$), the best lines or mixtures of phenotypically similar lines are typically tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

The modified single seed descent procedures involve harvesting multiple seed (i.e., a single lock or a simple boll) from each plant in a population and combining them to form a bulk. Part of the bulk is used to plant the next generation and part is put in reserve. This procedure has been used to save labor at harvest and to maintain adequate seed quantities of the population. The multiple-seed procedure may be used to save labor. It is considerably faster to gin bolls with a machine than to remove one seed by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, In: *Principles of plant breeding*, John Wiley & Sons, NY, University of California, Davis, Calif., 50-98, 1960; Simmonds, In: *Principles of crop improvement*, Longman, Inc., NY, 369-399, 1979; Sneep and Hendriksen, In: *Plant breeding perspectives*, Wageningen (Ed), Center for Agricultural Publishing and Documentation, 1979; Fehr, In: *Principles of variety development*, Theory and Technique (Vol 1) and Crop Species Soybean (Vol 2), Iowa State Univ., Macmillian Pub. Co., NY, 360-376, 1987; Fehr, In: *Soybeans: Improvement, Production and Uses,"* 2d Ed., *Manograph* 16:249, 1987). Additionally, with any of the methods disclosed above, mutagenesis can be utilized to increase the diversity of the gene pool that is available in the breeding program.

Proper testing should detect any major faults and establish the level of superiority or improvement over current varieties. In addition to showing superior performance, there must be a demand for a new variety that is compatible with industry standards or which creates a new market. The introduction of a new variety will incur additional costs to the seed producer, the grower, processor and consumer; for special advertising and marketing, altered seed and commercial production practices, and new product utilization. The testing preceding release of a new variety should take into consideration research and development costs as well as technical superiority of the final variety. For seed-propagated varieties, it must be feasible to produce seed easily and economically.

The two cotton species commercially grown in the United States are *Gossypium hirsutum*, commonly known as short staple or upland cotton and *Gossypium barbadense*, commonly known as extra long staple (ELS) or, in the United States, as Pima cotton. Upland cotton fiber is used in a wide array of coarser spin count products. Pima cotton is used in finer spin count yarns (50-80) which are primarily used in more expensive garments. Other properties of Pima cotton are critical because of fiber end use.

Cotton is an important and valuable field crop. Thus, a continuing goal of plant breeders is to develop stable, high yielding cotton varieties that are agronomically sound. The reasons for this goal are obviously to maximize the amount and quality of the fiber produced on the land used and to supply fiber, oil and food for animals and humans. To accomplish this goal, the cotton breeder must select and develop plants that have the traits that result in superior cultivars.

II. IMPROVEMENT OF COTTON VARIETIES

In certain further aspects, the invention provides plants modified to include at least a first desired trait. Such plants may, in one embodiment, be developed by a plant breeding technique called backcrossing, wherein essentially all of the desired morphological and physiological characteristics of a variety are recovered in addition to a genetic locus transferred into the hybrid via the backcrossing technique. The term backcrossing as used herein refers to the repeated crossing of a hybrid progeny back to a starting variety into which introduction of the desired trait is being carried out. The parental plant which contributes the locus or loci for the desired trait is termed the nonrecurrent or donor parent. This terminology refers to the fact that the nonrecurrent parent is used one time in the backcross protocol and therefore does not recur.

The parental cotton plant to which the locus or loci from the nonrecurrent parent are transferred is known as the recurrent parent as it is used for several rounds in the backcrossing protocol (Poehlman and Sleper, In: *Breeding Field Crops*, Iowa State University Press, Ames, 1995; Sprague and Dudley, In: *Corn and Improvement*, 3rd ed., 1988; Fehr, In: *Principles of variety development*, Theory and Technique (Vol 1) and Crop Species Soybean (Vol 2), Iowa State Univ., Macmillian Pub. Co., NY, 360-376, 1987b; Fehr, In: *Soybeans: Improvement, Production and Uses*," 2d Ed., *Manograph* 16:249, 1987). In a typical backcross protocol, the original line of interest (recurrent parent) is crossed to a second variety (nonrecurrent parent) that carries the genetic locus to be transferred. The resulting progeny from this cross are then crossed again to the recurrent parent and the process is repeated until a cotton plant is obtained wherein essentially all of the desired morphological and physiological characteristics of the recurrent parent are recovered in the converted plant, in addition to the transferred locus from the nonrecurrent parent.

The backcross process may be accelerated by the use of genetic markers, such as Simple Sequence Length Polymorphisms (SSLPs) (Williams et al., *Nucleic Acids Res.*, 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998) to identify plants with the greatest genetic complement from the recurrent parent.

The selection of a suitable recurrent parent is an important step for a successful backcrossing procedure. The goal of a backcross protocol is to add or substitute one or more new traits in a variety. To accomplish this, a genetic locus of the recurrent parent is modified or substituted with the desired locus from the nonrecurrent parent, while retaining essentially all of the rest of the desired genetic, and therefore the desired physiological and morphological constitution of the original plant. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, herbicide tolerance, resistance for bacterial, fungal, or viral disease, insect or nematode resistance, male sterility, ease of transformation, resistance to abiotic stresses and improved fiber characteristics. These genes are generally inherited through the nucleus, but may be inherited through the cytoplasm.

Direct selection may be applied where a genetic locus acts as a dominant trait. An example of a dominant trait is the herbicide tolerance trait. For this selection process, the progeny of the initial cross are sprayed with the herbicide prior to the backcrossing. The spraying eliminates any plants which do not have the desired herbicide tolerance characteristic, and only those plants which have the herbicide tolerance gene are used in the subsequent backcross. This process is then repeated for all additional backcross generations.

Many useful traits are those which are introduced by genetic transformation techniques. Methods for the genetic transformation of cotton are known to those of skill in the art, (see, e.g. Firoozabady et al., *Plant Mol. Biol.*, 10:105-116, 1987). For example, broadly applicable plant transformation methods which have been described include *Agrobacterium*-mediated transformation, microprojectile bombardment, electroporation, and direct DNA uptake by protoplasts.

*Agrobacterium*-mediated transfer is a widely applicable system for introducing gene loci into plant cells, including cotton. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio. Tech.*, 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio. Tech.*, 3(7):629-635, 1985; U.S. Pat. No. 5,563, 055). One efficient means for transformation of cotton in particular is transformation and regeneration of cotton hypocotyl explants following inoculation with *Agrobacterium tumefaciens* from primary callus development, embryogenesis, embryogenic callus identification, transgenic cotton shoot production and the development of transgenic plants, as is known in the art.

To effect transformation by electroporation, for example, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner. Protoplasts may also be employed for electroporation transformation of plants (Bates, *Mol. Biotechnol.*, 2(2):135-145, 1994; Lazzeri, *Methods Mol. Biol.*, 49:95-106, 1995). For example, the generation of transgenic cotyledon-derived protoplasts was described by Dhir and Widholm in Intl. Patent Appl. Publ. No. WO 92/17598, the disclosure of which is specifically incorporated herein by reference. When protoplasts are used, transformation can also be achieved using methods based on calcium phosphate precipitation, polyethylene glycol treatment, and combinations of these treatments (see, e.g., Potrykus et al., *Mol. Gen. Genet.*, 199(2):169-177, 1985; Omirulleh et al., *Plant Mol. Biol.*, 21(3):415-428, 1993; Fromm et al., *Nature*, 319(6056): 791-793, 1986; Uchimiya et al., *Mol. Gen. Genet.*, 204(2): 204-207, 1986; Marcotte and Bayley, *Nature*, 335(6189): 454-457, 1988).

Microprojectile bombardment is another efficient method for delivering transforming DNA segments to plant cells. In this method, particles are coated with nucleic acids and delivered into cells by a propelling force. Exemplary particles include those comprised of tungsten, platinum, and often, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

Microprojectile bombardment techniques are widely applicable, and may be used to transform virtually any plant species. The application of microprojectile bombardment for the transformation of cotton is described, for example, in Rajasekaran et al., *Mol. Breed.*, 2:307-319, 1996. An illustrative embodiment of a method for microprojectile bombardment is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

It is understood to those of skill in the art that a locus of transgenic origin need not be directly transformed into a plant, as techniques for the production of stably transformed cotton plants that pass single loci to progeny by Mendelian inheritance is well known in the art. Such single loci may therefore be passed from parent plant to progeny plants by standard plant breeding techniques that are well known in the art. Non-limiting examples of traits that may be introduced directly or by backcrossing are presented below.

A. Male Sterility

Male sterility genes can increase the efficiency with which hybrids are made, in that they eliminate the need to physically emasculate the plant used as a female in a given cross. Where one desires to employ male-sterility systems, it may be beneficial to also utilize one or more male-fertility restorer genes. For example, where cytoplasmic male sterility (CMS) is used, hybrid crossing requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Examples of male-sterility genes and corresponding restorers which could be employed with the plants of the invention are well known to those of skill in the art of plant breeding. Examples of such genes include CMS-D2-2, CMS-hir, CMS-D8, CMS-D4, and CMS-C1. Fertility can be restored to CMS-D2-2 by the D2 restorer in which the restorer factor(s) was introduced from the genome of *G. harknessii Brandegee* (D2-2). Microsporogenesis in both CMS systems aborts during the premeiotic stage. One dominant restorer gene from the D8 restorer was identified to restore fertility of CMS-D8. The D2 restorer for CMS-D2-2 also restores the fertility of CMS-D8, CMS-hir, and CMS-C1.

B. Herbicide Tolerance

Numerous herbicide tolerance genes are known and may be employed with the plants of the invention. An example is a gene conferring tolerance to a herbicide that inhibits the growing point or meristem, such as imidazalinone or sulfonylurea. Exemplary genes in this category code for mutant ALS and AHAS enzymes as described, for example, by Lee et al., *EMBO J.*, 7:1241, 1988; Gleen et al., *Plant Molec. Biology*, 18:1185-1187, 1992; Miki et al., *Theor. App. Genet.*, 80:449, 1990.

Tolerance genes for glyphosate (tolerance conferred by mutant 5-enolpyruvl-3 phosphikimate synthase (EPSPS and aroA genes) and hygromycin B phosphotransferase) and to other phosphono compounds such as glufosinate (phosphinothricin acetyl transferase (PAT) and *Streptomyces hygroscopicus* phosphinothricin-acetyl transferase (bar) genes) may also be used. For example, U.S. Pat. No. 4,940,835 to Shah, et al., discloses the nucleotide sequence of a form of EPSPS which can confer glyphosate tolerance. A DNA molecule encoding a mutant aroA gene can be obtained under ATCC accession number 39256, and the nucleotide sequence of the mutant gene is disclosed in U.S. Pat. No. 4,769,061 to Comai. A hygromycin B phosphotransferase gene from *E. coli* which confers resistance to glyphosate in tobacco callus and plants is described in Penaloza-Vazquez et al. (*Plant Cell Reports*, 14:482-487, 1995). European patent application No. 0 333 033 to Kumada et al., and U.S. Pat. No. 4,975,374 to Goodman et al., disclose nucleotide sequences of glutamine synthetase genes which confer tolerance to herbicides such as L-phosphinothricin. The nucleotide sequence of a phosphinothricin-acetyltransferase gene is provided in European application No. 0 242 246 to Leemans et al. DeGreef et al., (*Bio/Technology*, 7:61, 1989), describe the production of transgenic plants that express chimeric bar genes coding for phosphinothricin acetyl transferase activity. Exemplary genes conferring tolerance to herbicidal phenoxy propionic acids and cycloshexones, such as sethoxydim and haloxyfop are the Acct-S1, Acc1-S2 and Acct-S3 genes described by Marshall et al., (*Theor. App. Genet.*, 83:435, 1992). U.S. Patent Application No: 20030135879 describes isolation of a gene for dicamba monooxygenase (DMO) from *Psueodmonas maltophilia* which is involved in the conversion of a herbicidal form of the herbicide dicamba to a non-toxic 3,6-dichlorosalicylic acid and thus may be used for producing plants tolerant to this herbicide.

Genes are also known conferring tolerance to a herbicide that inhibits photosynthesis, such as triazine (psbA and gs+ genes) and benzonitrile (nitrilase gene). Przibilla et al., (*Plant Cell*, 3:169, 1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., (*Biochem. J.* 285:173, 1992). Protoporphyrinogen oxidase (PPO) is the target of the PPO-inhibitor class of herbicides; a PPO-inhibitor resistant PPO gene was recently identified in *Amaranthus tuberculatus* (Patzoldt et al., *PNAS*, 103(33): 12329-2334, 2006). The herbicide methyl viologen inhibits $CO_2$ assimilation. Foyer et al. (*Plant Physio.l*, 109:1047-1057, 1995) describe a plant overexpressing glutathione reductase (GR) which is resistant to methyl viologen treatment.

Siminszky (*Phytochemistry Reviews*, 5:445-458, 2006) describes plant cytochrome P450-mediated detoxification of multiple, chemically unrelated classes of herbicides.

Other examples of herbicide resistance have been described, for instance, in U.S. Pat. Nos. 6,803,501; 6,448,476; 6,248,876; 6,225,114; 6,107,549; 5,866,775; 5,804,425; 5,633,435; 5,463,175.

C. Disease Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., *Science*, 266:789, 1994 (cloning of the tomato Cf-9 gene for resistance to *Cladosporium fulvum*); Martin et al., *Science*, 262:1432, 1993 (tomato Pto gene for resistance to *Pseudomonas syringae* pv.); Mindrinos et al., *Cell*, 78:1089, 1994 (*Arabidopsis* RPS2 gene for resistance to *Pseudomonas syringae*). Logemann et al., (*Bio/technology*, 10:305, 1992), for example, disclose transgenic plants expressing a barley ribosome-inactivating gene have an increased resistance to fungal disease.

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.*, 28:451, 1990. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

A virus-specific antibody may also be used. See, for example, Tavladoraki et al., (*Nature*, 366:469, 1993), who show that transgenic plants expressing recombinant antibody genes are protected from virus attack. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or increasing salicylic acid production (Ryals et al., *Plant Cell*, 8:1809-1819, 1996).

Plant defensins may be used to provide resistance to fungal pathogens (Thomma et al., *Planta*, 216:193-202, 2002).

Nematode resistance has been described, for example, in U.S. Pat. No. 6,228,992 and bacterial disease resistance in U.S. Pat. No. 5,516,671.

D. Insect Resistance

One example of an insect resistance gene includes a *Bacillus thuringiensis* protein, a derivative thereof, or a synthetic polypeptide modeled thereon. See, for example, Geiser et al., (*Gene*, 48:109, 1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (*Plant Molec. Biol.*, 24:25, 1994), who disclose the nucleotide sequences of several *Clivia miniata* mannose-binding lectin genes. A vitamin-binding protein may also be used, such as avidin. See PCT application U.S. Ser. No. 93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., *J. Biol. Chem.*, 262: 16793, 1987 (nucleotide sequence of rice cysteine proteinase inhibitor), Huub et al., *Plant Molec. Biol.*, 21:985, 1993 (nucleotide sequence of cDNA encoding tobacco proteinase inhibitor I), and Sumitani et al., *Biosci. Biotech. Biochem.*, 57:1243, 1993 (nucleotide sequence of *Streptomyces nitrosporeus* α-amylase inhibitor).

An insect-specific hormone or pheromone may also be used. See, for example, Hammock et al., (*Nature*, 344:458, 1990) disclosing baculovirus expression of cloned juvenile hormone esterase, an inactivator of juvenile hormone, Gade and Goldsworthy (*Eds. Physiological System in Insects*, Elsevier Academic Press, Burlington, Mass., 2007), describing allostatins and their potential use in pest control; and Palli et al. (*Vitam. Horm.*, 73:59-100, 2005), disclosing use of ecdysteroid and ecdysteroid receptor in agriculture. The diuretic hormone receptor (DHR) was identified in Price et al. (Insect Mol. Biol., 13:469-480, 2004) as a candidate target of insecticides.

Still other examples include an insect-specific antibody or an immunotoxin derived therefrom and a developmental-arrestive protein. See Taylor et al., (Seventh Int'l Symposium on Molecular Plant-Microbe Interactions (Edinburgh, Scotland) Abstract #497, 1994), who described enzymatic inactivation in transgenic tobacco via production of single-chain antibody fragments.

E. Resistance to Abiotic Stresses

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, as described in U.S. Pat. No. 5,538,878 to Thomas et al.

F. Modified Fatty Acid, Phytate and Carbohydrate Metabolism

Genes may be used conferring modified fatty acid metabolism. For example, stearyl-ACP desaturase genes may be used. See Knutzon et al., *Proc. Natl. Acad. Sci. USA*, 89:2624, 1992. Various fatty acid desaturases have also been described, such as a *Saccharomyces cerevisiae* OLE1 gene encoding delta-9 fatty acid desaturase, an enzyme which forms the monounsaturated palmitoleic (16:1) and oleic (18:1) fatty acids from palmitoyl (16:0) or stearoyl (18:0) CoA (McDonough et al., *J. Biol. Chem.*, 267(9):5931-5936, 1992); a gene encoding a stearoyl-acyl carrier protein Δ9 desaturase from castor (Fox et al. *Proc. Natl. Acad. Sci. USA*, 90(6):2486-2490, 1993); Δ6 and Δ12 desaturases from the cyanobacteria *Synechocystis* responsible for the conversion of linoleic acid (18:2) to gamma-linolenic acid (18:3 gamma) (Reddy et al. *Plant Mol. Biol.*, 22(2):293-300, 1993); a gene from *Arabidopsis thaliana* that encodes an omega-3 desaturase (Arondel et al. *Science*, 258(5086):1353-1355, 1992); plant Δ9 desaturases (PCT Application Publ. No. WO 91/13972) and soybean and *Brassica* Δ15 desaturases (European Patent Application Publ. No. EP 0616644).

Phytate metabolism may also be modified by introduction of a phytase-encoding gene to enhance breakdown of phytate, adding more free phosphate to the transformed plant. For example, see Van Hartingsveldt et al., (*Gene*, 127:87, 1993), for a disclosure of the nucleotide sequence of an *Aspergillus niger* phytase gene. This, for example, could be accomplished by cloning and then reintroducing DNA associated with the single allele which is responsible for mutants characterized by low levels of phytic acid. See Raboy et al., (*Maydica*, 35:383, 1990).

A number of genes are known that may be used to alter carbohydrate metabolism. For example, plants may be transformed with a gene coding for an enzyme that alters the branching pattern of starch. See Shiroza et al., *J. Bacteol.*, 170:810, 1988 (nucleotide sequence of *Streptococcus mutans* fructosyltransferase gene), Steinmetz et al., *Mol. Gen. Genet.*, 20:220, 1985 (nucleotide sequence of *Bacillus subtilis* levansucrase gene), Pen et al., *BioTechnology*, 10:292, 1992 (production of transgenic plants that express *Bacillus licheniformis* α-amylase), Elliot et al., *Plant Molec. Biol.*, 21:515, 1993 (nucleotide sequences of tomato invertase genes), Sergaard et al., *J. Biol. Chem.*, 268:22480, 1993 (site-directed mutagenesis of barley α-amylase gene), and Fisher et al., *Plant Physiol.*, 102:1045, 1993 (maize endosperm starch branching enzyme II). The Z10 gene encoding a 10 kD zein storage protein from maize may also be used to alter the quantities of 10 kD Zein in the cells relative to other components (Kirihara et al., *Mol. Gen. Genet.*, 211:477-484, 1988).

G. Improved Cotton Fiber Characteristics

Fiber characteristics such as fiber quality of quantity represent another example of a trait that may be modified in cotton varieties. For example, U.S. Pat. No. 6,472,588 describes transgenic cotton plants transformed with a sucrose phosphate synthase nucleic acid to alter fiber characteristics such as strength, length, fiber fineness, fiber maturity ratio, immature fiber content, fiber uniformity, and micronaire. Cotton plants comprising one or more genes coding for an enzyme selected from the group consisting of endoxyloglucan transferase, catalase and peroxidase for the improvement of cotton fiber characteristics are also described in U.S. Pat. No. 6,563,022. Cotton modification using ovary-tissue transcriptional factors preferentially directing gene expression in ovary tissue, particularly in very early fruit development, utilized to express genes encoding isopentenyl transferase in cotton ovule tissue and modify the characteristics of boll set in cotton plants and alter fiber quality characteristics including fiber dimension and strength is discussed in U.S. Pat. No. 6,329,570. A gene controlling the fiber formation mechanism in cotton plants is described in U.S. Pat. No. 6,169,174.

Genes involved in lignin biosynthesis are described by Dwivedi et al., Mol. Biol., 26:61-71, 1994; Tsai et al., *Physiol.*, 107:1459, 1995; U.S. Pat. No. 5,451,514 (claiming the use of cinnamyl alcohol dehydrogenase gene in an antisense orientation such that the endogenous plant cinnamyl alcohol dehydrogenase gene is inhibited).

H. Additional traits

Additional traits can be introduced into the cotton variety of the present invention. A non-limiting example of such a trait is a coding sequence which decreases RNA and/or protein levels. The decreased RNA and/or protein levels may be achieved through RNAi methods, such as those described in U.S. Pat. No. 6,506,559 to Fire and Mellow.

Another trait that may find use with the cotton variety of the invention is a sequence which allows for site-specific recombination. Examples of such sequences include the FRT sequence, used with the FLP recombinase (Zhu and Sadowski, *J. Biol. Chem.*, 270:23044-23054, 1995); and the LOX sequence, used with CRE recombinase (Sauer, *Mol. Cell. Biol.*, 7:2087-2096, 1987). The recombinase genes can be encoded at any location within the genome of the cotton plant, and are active in the hemizygous state.

It may also be desirable to make cotton plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews*, 67:16-37, 2003).

III. TISSUE CULTURES AND IN VITRO REGENERATION OF COTTON PLANTS

A further aspect of the invention relates to tissue cultures of the cotton variety designated 11R124B2R2. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, and the like. In one embodiment, the tissue culture comprises embryos, protoplasts, meristematic cells, pollen, leaves or anthers.

An important ability of a tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Plants typically are regenerated via two distinct processes; shoot morphogenesis and somatic embryogenesis. Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos. Lines that produce large numbers of embryos during an induction step may not give rise to rapidly-growing proliferative cultures. Therefore, it may be desired to optimize tissue culture conditions for each cotton line. These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it allows a single, transformed cell to multiply to the point that it will contribute to germ-line tissue.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

IV. DEFINITIONS

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Desired Agronomic Characteristics: Agronomic characteristics (which will vary from crop to crop and plant to plant) such as yield, maturity, pest resistance and lint percent which are desired in a commercially acceptable crop or plant. For example, improved agronomic characteristics for cotton include yield, maturity, fiber content and fiber qualities.

Diploid: A cell or organism having two sets of chromosomes.

Disease Resistance: The ability of plants to restrict the activities of a specified pest, such as an insect, fungus, virus, or bacteria.

Disease Tolerance: The ability of plants to endure a specified pest (such as an insect, fungus, virus or bacteria) or an adverse environmental condition and still perform and produce in spite of this disorder.

Donor Parent: The parent of a variety which contains the gene or trait of interest which is desired to be introduced into a second variety.

ELS: The abbreviation for "Extra Long Staple." ELS is the group classification for cotton in the longest staple length category. As used in practice and for commerce, ELS denotes varieties belonging to the species *G. barbadense* that have superior fiber qualities, including classification in the longest staple length category.

Emasculate: The removal of plant male sex organs or the inactivation of the organs with a cytoplasmic or nuclear genetic factor conferring male sterility or a chemical agent.

Essentially all of the physiological and morphological characteristics: A plant having essentially all of the physiological and morphological characteristics of a designated plant has all of the characteristics of the plant that are otherwise present when compared in the same environment, other than an occasional variant trait that might arise during backcrossing or direct introduction of a transgene.

$F_1$ Hybrid: The first generation progeny of the cross of two nonisogenic plants.

Fallout (Fo): As used herein, the term "fallout" refers to the rating of how much cotton has fallen on the ground at harvest.

2.5% Fiber Span Length: Refers to the longest 2.5% of a bundle of fibers expressed in inches as measured by a digital fibergraph.

Fiber Characteristics: Refers to fiber qualities such as strength, fiber length, micronaire, fiber elongation, uniformity of fiber and amount of fiber.

Fiber Elongation: Sometimes referred to as E1, refers to the elongation of the fiber at the point of breakage in the strength determination as measured by High Volume Instrumentation (HVI).

Fiber Span Length: The distance spanned by a specific percentage of fibers in a test specimen, where the initial starting point of the scanning in the test is considered 100 percent as measured by a digital fibergraph.

Fiber Strength: Also referred to as T1, denotes the force required to break a bundle of fibers. Fiber strength is expressed in millinewtons (mn) per tex on a stelometer.

Fruiting Nodes: The number of nodes on the main stem from which arise branches that bear fruit or boll in the first position.

Genotype: The genetic constitution of a cell or organism.

Gin Turnout: Refers to fraction of lint in a machine harvested sample of seed cotton (lint, seed, and trash).

Haploid: A cell or organism having one set of the two sets of chromosomes in a diploid.

Linkage: A phenomenon wherein alleles on the same chromosome tend to segregate together more often than expected by chance if their transmission was independent.

Lint Index: The weight of lint per seed in milligrams.

Lint Percent: Refers to the lint (fiber) fraction of seed cotton (lint and seed).

Lint Yield: Refers to the measure of the quantity of fiber produced on a given unit of land. Presented herein in pounds of lint per acre.

Lint/boll: As used herein, the term "lint/boll" is the weight of lint per boll.

Maturity Rating: A visual rating near harvest on the amount of open bolls on the plant. The rating range is from 1 to 5, 1 being early and 5 being late.

Micronaire: A measure of the fineness of the fiber. Within a cotton cultivar, micronaire is also a measure of maturity. Micronaire differences are governed by changes in perimeter or in cell wall thickness, or by changes in both. Within a variety, cotton perimeter is fairly consistent and maturity will cause a change in micronaire. Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about 2.0 to 6.0:

Phenotype: The detectable characteristics of a cell or organism, which characteristics are the manifestation of gene expression.

Plant Height: The average height in meters of a group of plants.

Quantitative Trait Loci (QTL): Quantitative trait loci (QTL) refer to genetic loci that control to some degree numerically representable traits that are usually continuously distributed.

Recurrent Parent: The repeating parent (variety) in a backcross breeding program. The recurrent parent is the variety into which a gene or trait is desired to be introduced.

Regeneration: The development of a plant from tissue culture.

Seed/boll: Refers to the number of seeds per boll.

Seedcotton/boll: Refers to the weight of seedcotton per boll.

Seedweight: Refers to the weight of 100 seeds in grams.

Self-pollination: The transfer of pollen from the anther to the stigma of the same plant or a plant of the same genotype.

Single Locus Converted (Conversion) Plant: Plants which are developed by a plant breeding technique called backcrossing wherein essentially all of the desired morphological and physiological characteristics of a variety are recovered in addition to the characteristics conferred by the single locus transferred into the variety via the backcrossing technique. A single locus may comprise one gene, or in the case of transgenic plants, one or more transgenes integrated into the host genome at a single site (locus).

Stringout Rating: also sometimes referred to as "Storm Resistance" refers to a visual rating prior to harvest of the relative looseness of the seed cotton held in the boll structure on the plant. The rating values are from 1 to 5 (tight to loose in the boll).

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a cotton plant by transformation.

Uniformity Ratio: A measure of the relative fiber span length uniformity of a bundle of fibers. The uniformity ratio is determined by dividing the 50% fiber span length by the 2.5% fiber span length.

Vegetative Nodes: The number of nodes from the cotyledonary node to the first fruiting branch on the main stem of the plant.

V. DEPOSIT INFORMATION

Applicant has made a deposit of at least 2500 seeds of cotton variety 11R124B2R2 disclosed herein with the American Type Culture Collection (ATCC), 10801 University Boulevard, Manassas, Va. 20110-2209 USA. The accession number for the deposit is ATCC Accession No. PTA-122008 and the date of deposit was Feb. 18, 2015. Access to this deposit will be available during the pendency of the application to the Commissioner of Patents and Trademarks and persons determined by the Commissioner to be entitled thereto upon request. The deposit will be maintained for a period of 30 years, or 5 years after the most recent request, or for the enforceable life of the patent, whichever is longer, and will be replaced if it becomes nonviable during that period. Applicant does not waive any infringement of rights granted under this patent or under the Plant Variety Protection Act (7 U.S.C. 2321 et seq.).

The references cited herein, to the extent that they provide exemplary procedural or other details supplementary to those set forth herein, are specifically incorporated herein by reference.

What is claimed is:

1. A plant of cotton variety 11R124B2R2, wherein a sample of seed of said variety has been deposited under ATCC Accession No. PTA-122008.

2. A plant part of the plant of claim 1, wherein the plant part comprises at least a first cell of said plant.

3. The plant part of claim 2, further defined as pollen, a meristem, a cell, or an ovule.

4. A seed of cotton variety 11R124B2R2, wherein a sample of seed of said variety has been deposited under ATCC Accession No. PTA-122008.

5. A cotton plant that expresses all of the physiological and morphological characteristics of cotton variety 11R124B2R2, wherein a sample of seed of said variety has been deposited under ATCC Accession No. PTA-122008.

6. A method of producing cotton seed, wherein the method comprises crossing the plant of claim 1 with itself or a second, distinct cotton plant.

7. The method of claim 6, wherein the method comprises crossing the plant of cotton variety 11R124B2R2 with a second, distinct cotton plant to produce an $F_1$ hybrid cotton seed.

8. An $F_1$ hybrid cotton seed produced by the method of claim 7.

9. An $F_1$ hybrid cotton plant produced by growing the seed of claim 8.

10. A composition comprising a seed of cotton variety 11R124B2R2 comprised in plant seed growth media, wherein a sample of seed of said variety has been deposited under ATCC Accession No. PTA-122008.

11. The composition of claim 10, wherein the growth media is soil or a synthetic cultivation medium.

12. A plant produced by introducing a single locus conversion into cotton variety 11R124B2R2, or a selfed progeny thereof comprising the single locus conversion, wherein the single locus conversion was introduced into cotton variety 11R124B2R2 by backcrossing or genetic transformation and wherein a sample of seed of cotton variety 11R124B2R2 has been deposited under ATCC Accession No. PTA-122008.

13. The plant of claim 12, wherein the single locus conversion comprises a transgene.

14. A seed that produces the plant of claim 12.

15. The seed of claim 14, wherein the single converted locus confers a trait selected from the group consisting of male sterility, herbicide tolerance, insect or pest resistance, disease resistance, modified fatty acid metabolism, abiotic stress resistance, a sequence which allows for site-specific genetic recombination, modified carbohydrate metabolism and modified cotton fiber characteristics.

16. The seed of claim 15, wherein the single converted locus confers tolerance to an herbicide selected from the group consisting of glyphosate, sulfonylurea, imidazolinone, dicamba, glufosinate, phenoxy propionic acid, cyclohexanedione, triazine, benzonitrile and bromoxynil.

17. The seed of claim 15, wherein the trait is insect resistance and said single converted locus comprises of a transgene encoding a *Bacillus thuringiensis* (Bt) endotoxin.

18. The seed of claim 14, wherein the single locus conversion comprises a transgene.

19. The method of claim 7, wherein the method further comprises:
   (a) crossing a plant grown from said $F_1$ hybrid cotton seed with itself or a different cotton plant to produce a seed of a progeny plant of a subsequent generation;
   (b) growing a progeny plant of a subsequent generation from said seed of a progeny plant of a subsequent generation and crossing the progeny plant of a subsequent generation with itself or a second plant to produce a progeny plant of a further subsequent generation; and
   (c) repeating steps (a) and (b) using said progeny plant of a further subsequent generation from step (b) in place of the plant grown from said $F_1$ hybrid cotton seed in step (a), wherein steps (a) and (b) are repeated with sufficient inbreeding to produce an inbred cotton plant derived from the cotton variety 11R124B2R2.

20. The method of claim 19, further comprising crossing said inbred cotton plant derived from the cotton variety 11R124B2R2 with a plant of a different genotype to produce a seed of a hybrid cotton plant derived from the cotton variety 11R124B2R2.

21. A method of producing a commodity plant product comprising collecting the commodity plant product from a plant of cotton variety 11R124B2R2, wherein a sample of seed of said variety has been deposited under ATCC Accession No. PTA-122008.

22. The method of claim 21, wherein the commodity plant product is lint, seed oil, or seed.

* * * * *